United States Patent [19]

Walsh et al.

[11] 4,162,279
[45] Jul. 24, 1979

[54] PHOSPHONOXYCARBOXAMIDES

[75] Inventors: Edward N. Walsh, New City; Ralph B. Fearing, Bardonia, both of N.Y.

[73] Assignee: Stauffer Chemical Company, Westport, Conn.

[21] Appl. No.: 837,072

[22] Filed: Sep. 28, 1977

[51] Int. Cl.² ............................ C07F 9/11; C07F 9/40
[52] U.S. Cl. ...................... 260/943; 252/8.1; 427/372 R
[58] Field of Search .......................... 260/943

[56] References Cited

U.S. PATENT DOCUMENTS

| | | | |
|---|---|---|---|
| 2,494,283 | 1/1950 | Cassaday et al. | 260/943 |
| 3,032,579 | 5/1962 | Losco et al. | 260/943 |
| 3,057,774 | 10/1962 | Baker et al. | 260/943 |
| 3,268,292 | 8/1966 | Chance et al. | 8/116.3 |
| 3,374,292 | 3/1968 | Zahir | 260/943 |
| 3,556,840 | 1/1971 | Tesoro | 117/137 |
| 3,763,283 | 10/1973 | Curgan | 260/938 |
| 3,835,204 | 9/1974 | Weil | 260/938 |

OTHER PUBLICATIONS

Shishkin et al., "J. of Gen. Chem. of U.S.S.R.", vol. 46, No. 10, Part 1, pp. 2143–2146.
Shishkin et al., "J. of Gen. Chem. of U.S.S.R.", vol. 44, pp. 504–508, English Translation, Mar. 1974.

*Primary Examiner*—Anton H. Sutto
*Attorney, Agent, or Firm*—William C. Gerstenzang

[57] ABSTRACT

Novel phosphonoxycarboxamides of the formula:

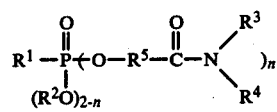

wherein $R^1$ and $R^2$ are selected from the group consisting of aryl and alkyl having from 1–6 carbon atoms and may be the same or different; $R^3$ represents hydrogen or —CH$_2$OH; $R^4$ represents hydrogen, —CH$_3$, —CH$_2$OH, or —C$_2$H$_4$OH, $R^5$ represents an alkyl group having from 1–5 carbon atoms; and n represents 1 or 2 are useful as flame retardant agents for textile materials.

6 Claims, No Drawings

PHOSPHONOXYCARBOXAMIDES

TECHNICAL DISCLOSURE

This invention relates to new and useful phosphonoxycarboxamides and their method of preparation. More particularly, this invention relates to new phosphonoxycarboxamide compounds which are useful as agents for imparting flame retardance to textile materials such as cotton fabric or yarn.

It has long been known that flame retardant properties may be incorporated into textile materials such as cotton fabric or yarn by treatment with phosphorus-containing compounds. Such compounds are usually in the form of organophosphorus compounds which are relatively harmless to the material being treated as well as resistant to laundering.

More recently, it has been discovered that organic nitrogen is a synergist for phosphorus-induced flame retardance in cellulosic fabrics, and its presence in the flame-retardant compound permits a reduction in the amount of flame retardant which is required to achieve an acceptable degree of flame retardance. Exemplary of flame-retardant compounds which contain both nitrogen and phosphorus are those disclosed in U.S. Pat. Nos. 3,268,292; 3,374,292; 3,556,840; 3,634,422; 3,763,283; and 3,835,204.

It is an object of this invention to provide a novel class of phosphonoxycarboxamide compounds which are effective in imparting flame retardance to textile materials. It is another object of this invention to provide novel compositions which may be used at relatively low add-on weights to impart flame retardance to textile compositions. It is a further object of this invention to provide a novel process by which flame retardancy may be imparted to textile materials.

In accordance with one aspect of this invention, there is provided a compound of the formula:

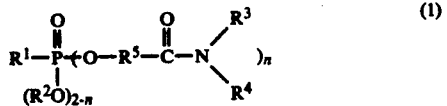
(1)

wherein $R^1$ and $R^2$ are selected from the group consisting of aryl and alkyl having from 1-6 carbon atoms and may be the same or different; $R^3$ represents hydrogen or $-CH_2OH$; $R^4$ represents hydrogen, $-CH_3$, $-CH_2OH$, or $-C_2H_4OH$, $R^5$ represents an alkyl group having from 1-5 carbon atoms, provided that only one of $R^3$ and $R^4$ may be hydrogen; and n represents 1 or 2.

Within the broad class of compounds encompassed by this invention, a particularly preferred subclass comprises those compounds wherein $R^1$ represents an alkyl radical of from 1-4 carbon atoms; $R^2$ represents an alkyl radical of from 1-2 carbon atoms; $R^3$ represents hydrogen or $-CH_2OH$; $R^4$ represents hydrogen, $-CH_3$, $-CH_2OH$, or $-CH_2CH_2OH$, $R^5$ represents $-CH_2$; and n represents 1 or 2.

In accordance with another aspect of this invention, there is provided a flame-retardant composition comprising: (1) at least one compound represented by the formula:

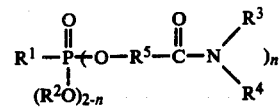

wherein $R^1$ and $R^2$ are selected from the group consisting of aryl and alkyl having from 1-6 carbon atoms and may be the same or different; $R^3$ represents hydrogen or $-CH_2OH$; $R^4$ represents hydrogen, $-CH_3$, $-CH_2OH$, or $-C_2H_4OH$, $R^5$ represents an alkyl group having from 1-5 carbon atoms; and n represents 1 r 2; (2) an aminoplast; and (3) an acid catalyst. In preferred embodiments, the flame-retardant composition is an aqueous formulation wherein the aminoplast is present at a concentration ranging from about 10 to about 600 percent by weight of the phosphonoxycarboxamide compound, the acid catalyst is present at a concentration ranging from about 0.01 to about 5 percent by weight of the phosphonoxycarboxamide, and the total concentration (i.e., the "solids" content) of the phosphonoxycarboxamide, aminoplast, and catalyst is adjusted to provide a phosphorus uptake of 1 to 5% by weight on the fabric being treated.

In accordance with a further aspect of this invention, there is provided a process for imparting flame retardance to textile materials comprising the steps of impregnating the textile material with a flame-retardant composition comprising: (a) at least one compound represented by the formula:

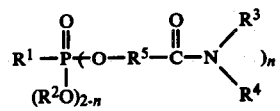

wherein $R^1$ and $R^2$ are selected from the group consisting of aryl and alkyl having from 1-6 carbon atoms and may be the same or different; $R^3$ represents hydrogen or $-CH_2OH$; $R^4$ represents hydrogen, $-CH_3$, $-CH_2OH$, or $-C_2H_4OH$; $R^5$ represents an alkyl group having from 1-5 carbon atoms; and n represents 1 or 2; (b) an aminoplast; and (c) an acid catalyst and heating the impregnated textile material to a temperature sufficient to cure the flame-retardant composition.

The phosphonoxycarboxamides of this invention may be prepared by a variety of techniques known in the art. For example, when n=1, they may be prepared by reacting a carbalkoxy alkyl phosphonate such as a carbalkoxy methyl phosphonate, i.e.,

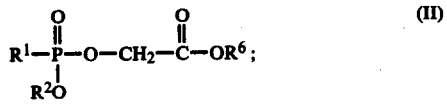
(II)

wherein $R^1$ and $R^2$ are as defined hereinabove, and $R^6$ represents an alkyl group having from 1 to 2 carbon atoms; with ammonia, i.e., $NH^3$ to form an N- unsubstituted phosphonoxycarboxamide

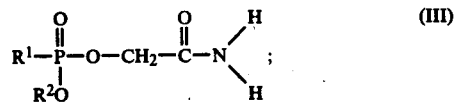
(III)

or with a primary amine such as, for example, methyl amine, ethanolamine, or the like to form a partially N-substituted phosphonoxycarboxamide, e.g.,

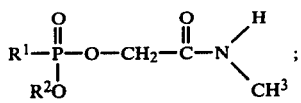

or

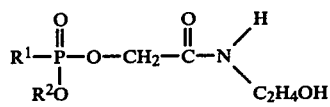

This reaction may be conducted in a solvent which is nonreactive towards either the starting reagents or the resulting phosphonoxycarboxamide. Suitable solvents include, but are not limited to water, methanol, ethanol, ethylene glycol, diethyl ether, acetone, toluene, and the like, The reaction is conducted at a temperature ranging from about 0° C. to about 40° C. and generally requires a reaction time ranging from about 2 to 20 hours.

The phosphonoxy-bis-carboxamide compounds (i.e., Compound I wherein n=2) of this invention may be prepared using the same procedures as described above except that a bis-carbalkoxyalkyl phosphonate, i.e.,

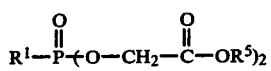

is used as a starting material instead of a carbalkoxymethyl phosphonate (II).

The precursor phosphonates (Compounds II and IIA) used in preparing the novel phosphonoxyacetamides of this invention may be prepared by reacting an alkyl, aryl, alkylaryl, or arylalkyl phosphonate with an alkyl halo alkanoate at a temperature ranging from about 125° C. to about 175° C. in the presence of an anionic catalyst such as sodium carbonate at a concentration ranging from about 0.2 percent to about 0.5 percent by weight of total reaction mixture. This reaction is generally conducted without a solvent and requires from about 8 to about 12 hours at the stated temperature range. Typical alkyl phosphonates which may be used in preparing these precursor phosphonates include, but are not limited to, dimethyl methylphosphonate, diethyl methyphosphonate, dimethyl ethylphosphonate, diethyl ethylphosphonate, dimethyl butylphosphonate, dipropyl butylphosphonate, dibutyl butylphosphonate, and the like.

Exemplary of the alkyl halo alkanoates which may be used to form the precursor phosphonate compounds are methyl chloroacetate, ethyl chloroacetate, ethylbromoacetate, and the like.

Thus, the formation of precursor phosphonates II and IIA may be illustrated schematically as follows.

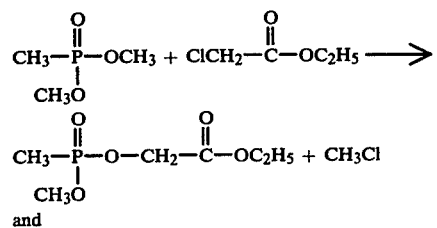

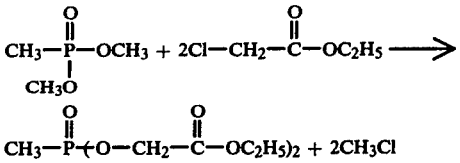

The N- unsubstituted or partially substituted phosphonoxycarboxamides which are prepared by reacting the precursor phosphonates with either ammonia or a primary amine may then be condensed with an aldehyde to form the alkyloamides. Aldehydes which may be used for this purpose include, but are not limited to, formaldehyde, acetaldehyde, and glyoxal. The alkylolamides may then be reacted with an aminoplast to form a water-insoluble resin. Aminoplasts which may be used for this purpose include, but are not limited to, methylol- and methoxymethylmelamines, methylolated ureas, and cyclic ureas such as dimethyloldihydroxyethyleneurea.

For example, Compound III may be methylolated by reaction with formaldehyde, which can be in gaseous, liquid solution, or solid form, over a period of from about 0.5 to about 2 hours at a temperature ranging from about 55° to about 85° C. while maintaining the system at an alkaline pH, preferably in the range of about 7.5 to about 8.5. The product of this reaction using Compound III will be a mixture of the monomethylol substituted derivative (V) and the dimethylol derivative (VI):

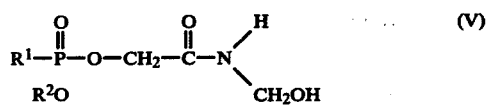

and

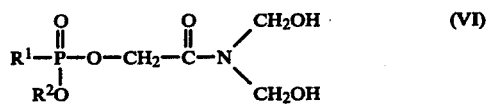

wherein the specific proportions of the mono- and dimenthylol derivatives within the mixture depends, in part, upon the molar ratio of the formaldehyde relative to the unsubstituted phosphonoxycarboxamide present in the initial reaction mixture. Although completely satisfactory in this form for most applications, it is understood that, if desired, the reaction product may be further refined by techniques well-known in the art to obtain the desired compound in a more pure form such as, for example, by crystallization.

The partially substituted phosphonoxycarboxamides (i.e., Compounds IVA, IVB) may also be reacted with formaldehyde to form N-methylol substituted derivatives, i.e.,

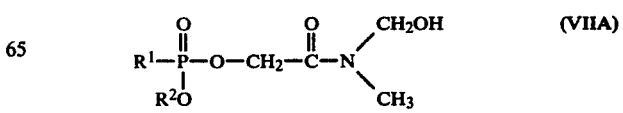

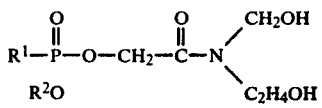 (VIIB)

Exemplary phosphonoxycarboxamides of this invention are: O-methyl methylphosphonoxyacetamide:

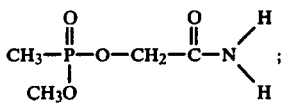 (1)

N-methylol, O-methyl methylphosphonoxyacetamide:

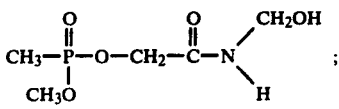 (2)

N-methyl-N-methylol. O-methyl methylphosphonoxyacetamide:

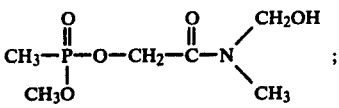 (3)

N,N-dimethylol, O-methyl methylphosphonoxyacetamide:

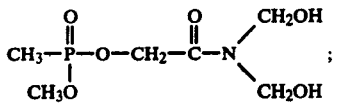 (4)

O-methyl ethylphosphonoxyacetamide:

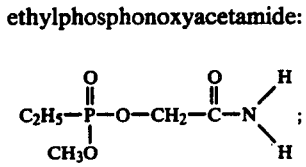 (5)

O-ethyl ethylphosphonoxyacetamide:

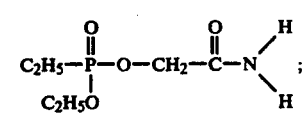 (6)

N-methylol, O-ethyl ethylphosphonoxyacetamide:

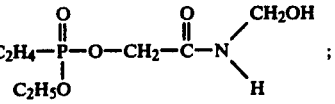 (7)

N-methyl, N-hydroxyethyl, O-ethyl ethylphosphonoxyacetamide:

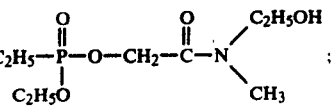 (8)

Bis (carbamidomethyl) methylphosphonate:

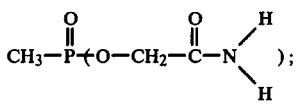 (9)

Bis (carbamidomethyl) ethyl phosphonate:

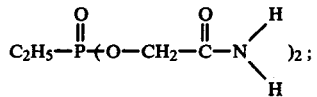 (10)

Bis (dimethylol carbamidomethyl) ethyl phosphonate:

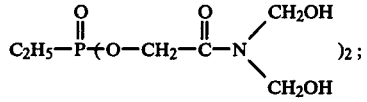 (11)

Bis (N-methyl-N-methylol carbamidomethyl) methylphosphonate:

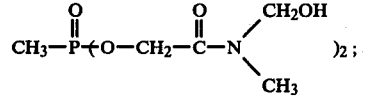 (12)

The unsubstituted phosphonoxycarboxamides of structure (III) and the partially substituted phosphonoxycarboxamides of structure (IV) are useful in their own right since they can be bonded to a textile by means of a reaction with an aminoplast. Thus, for example, a compound of structure (III) such as is illustrated by O-methyl methylphosphonoxyacetamide can be admixed with about 0.2 to 5 parts by weight of tri-, tetra-, or pentamethylolated melamine, or a partially etherified derivative thereof, and cured in the presence of an acid catalyst such as those hereinabove described so as to yield durable flame retardant finishes on cellulosic, cellulosepolyester, or other textiles. Methylolation of the phosphonoxycarboxamide does, however, offer the advantage of making it reactive with cellulose as well as with the aminoplast and thus generally minimizes the amount of aminoplast which is required.

The phosphonoxycarboxamides of this invention may be applied to normally flammable substrates in the form of an aqueous flame retardant formulation or as a liquid formulation in any of the organic solvents commonly used in the solvent finishing of textiles including, for example, ethanol, methanol, chloroform, water and mixtures thereof. Preferably, these formulations also include an aminoplast and an acid catalyst.

The term "aminoplast" is here meant to denote a nitrogen-containing resin which is capable of reacting with itself, with the phosphonoxycarboxamide, and/or with the textile or other substrate, and which is prepared by the polycondensation of formaldehyde with a compound having at least two reactive amino or amido hydrogen atoms. Exemplary of the aminoplasts which may be used are methylolureas which may be either straight chained or cyclic, methylolmelamines, methylolcarbamates, methylolurons, methylolamides, the methyl ethers of the above listed methylol compounds, methylolated acid amides, urea glyoxal condensation products, urea-glyoxalformaldehyde condensation products, N-methylolated or N,N-dimenthylolated O-alkyl, O-alkoxy, or O-hydroxyalkyl carbamates. Preferred aminoplasts include tris(methoxymethyl) melamine as sold by the American Cyanamid Company under the trademark "AEROTEX M-3"; partially methylated melamine as sold by the American Cyanamid Company under the trademark "AEROTEX 23 SPECIAL"; demethylolethylene urea; dimethylol dihydroxyethylene urea, dimethylol methyl carbamate, dimethylol hydroxyethyl/hydroxypropyl carbamate, and dimethoxymethyl uron. For most purposes, the use of one or more of the above-described aminoplasts at a concentration ranging from 10 to 600 percent and preferably from about 25 to 300 percent by weight of the phosphonoxyacetamide will be satisfactory.

Suitable acidic catalysts for use in the flame-retardant compositions of this invention include mineral acids such as phosphoric acid; organic acids such as oxalic, citric, succinic, maleic, glycolic, chloroacetic, and toluenesulfonic acids; alkyl acid phosphates, and the like. Also included are the salts of strong acids with relatively weak bases such as, for example, zinc nitrate, zinc chloride, magnesium chloride, ammonium chloride, ammonium phosphates, and amine hydrochlorides. Some typical amine hydrochlorides include 2-amino-2-methylpropanol hydrochloride sold under the tradename "Catalyst AC" by the Monosanto Company, and the alkanolamine hydrochloride sold as "Catalyst XRF" by the Millmaster Onyx Corporation. The use of one or more of these catalysts in a concentration of from about 0.01 to 5 percent based on the weight of the phosphonoxyacetamide will be suitable for most purposes.

The concentration (i.e., the "solids" content) of the phosphonoxycarboxamide/aminoplast/catalyst composition used may vary in accordance with several factors such as the nature of the substrate or fabric to which it is being applied, the amount of phosphonoxycarboxamide resin desired in or on the final product, and the like. It is generally desirable, however, to achieve a phosphorous uptake on the textile or other substrate ranging from about 1 to about 5 percent by weight of the dry untreated fabric or substrate. Thus, the concentration of the flame-retardant composition will be adjusted to a solids level which will produce the desired amount of phosphorous uptake with the anticipated amount of wet-pickup. The ranges given, of course, are merely illustrative and may be varied in accordance with the particular needs of the user.

The flame-retardant composition containing the phosphonoxycarboxamide, aminoplast, and catalyst may be applied to textiles or other substrates by the use of any of those techniques known in the art for this purpose such as dipping, spraying, painting, padding, etc. A preferred method for applying the composition to a fabric is that known as "padding" wherein the fabric is passed or "padded" through the composition while the latter is being held in a tank or other suitable container. For most applications, it is desirable to maintain the pH of the padding bath in the range of from about 4.5 to about 5.5.

The thus applied flame-retardant composition may then be dried and cured. Drying may be accomplished by various techniques including heating at a temperature ranging from room temperature up to about 120° C. or higher. It is, of course, entirely possible to eliminate drying as a separate step and accomplish the drying as a part of the curing step. Curing may be accomplished by heating at a temperature ranging from about 130° C. to about 180° C. with temperatures in the range of from about 150° to 160° C. being preferred. Curing time may vary from about 1 minute to about 20 minutes depending on the nature of the substrate being treated. The effect of the curing operation is to cause the alkylolated phosphonoxycarboxamide and aminoplast to react with the cellulose or with each other so as to form a cross-linked, insoluble finish in and/or on the individual fibers comprising the textile or other flammable structure.

As used herein, the term "flame retardant" is intended to refer to that particular property of a material which provides it with a degree of resistance to ignition and burning. Thus, a fire or flame retardant textile, paper, or other solid substrate is one which has a low level of flammability and flame spread. This property may be conveniently evaluated by means of any of the standard flame retardancy tests such as, for example, the vertical char length tests described in the federal Flammability Standard of July 27, 1971 (35 *Federal Register* 146).

As used herein, the term "textile" or "textiles" is meant to encompass woven or knitted fabrics as well as nonwoven fabrics which consist of continuous or discontinuous fibers bonded so as to form a fabric by mechanical entanglement, thermal interfiber bonding, or by use of adhesive or bonding substances. Such nonwoven fabrics may contain a certain percentage, up to 100 percent, of wood pulp as well as conventional textile fibers in which case part of the bonding process is achieved by means of hydrogen bonding between the cellulosic pulp fibers. In non-woven fabrics, the compounds of this invention can serve not only as flame retardant finishes but can also contribute to the interfiber bonding mechanism by serving as all or part of the adhesive or bonding resin component. This dual role can also be played by the phosphonoxycarboxamides of this invention in fabric laminates where they can at the same time serve as the interlaminar bonding agent and as the flame retardant. In both of these systems, i.e., non-woven fabrics and laminated fabrics, the compounds of this invention can also be blended with the usual bonding agents such as, for example, acrylic enulsion polymers, vinyl acetate homo- and copolymer emulsions, styrenebutadiene rubber emulsions, urethane resin emulsions, polyvinyl chloride emulsions, vinyl chloride-alkyl acrylate copolymer emulsions, polyacrylates modified by vinyl carboxylic acid comonomers, and the like.

The preparation and use of the novel phosphonoxycarboxamide compounds of this invention is further illustrated by the following nonlimiting examples, all parts and percentages given being by weight unless otherwise stated.

EXAMPLE 1

This example illustrates the preparation of O-methyl O-carbomethoxymethyl methylphosphonate to be used as a precursor in preparing the phosphonoxycarboxamides of this invention.

1118 grams (9 moles) of dimethyl methylphosphonate was mixed with 653.5 grams (6 moles) methyl chloroacetate and 4.0 grams sodium carbonate (catalyst) in a flask equipped with a stirrer, an overhead condenser, and a condensate trap. The reaction mixture was heated over several hours to a temperature of 128° C. during which period some methyl chloride was collected in the condensate trap. The reaction mixture was brought to a temperature of 130°–131° C. and held there for several hours during which time 239 grams of methyl chloride was collected in the distillate trap. Increasing the temperature to 138° C. for one hour produced an additional 28 grams of methyl chloride.

The reaction product was then stripped in a 1-foot vigreux column to remove excess dimethyl methylphosphonate. A first distillate fraction, weighing 509.5 grams, was taken off at a column pressure of 24 mm. Hg. abs., a base temperature of up to 119° C., and an overhead vapor temperature of up to 87° C.; and a second distillate fraction, weighing 150 grams, was taken off at a column pressure of 0.1 mm. Hg. abs., a base temperature up to 100° C., and an overhead vapor temperature up to 40° C. The total amount of distillate collected, 659.5 grams, exceeded the theoretical amount by 123.5 grams. This excess was attributed to unsubstituted dimethyl methylphosphate remaining in the reaction mixture due to the disubstitution of a corresponding amount of the desired product by an extra mole of methyl chloroacetate.

The crude reaction product remaining after distillation had an acidity to bromothymol blue equivalent to 0.18 milliequivalents acid per gram.

EXAMPLE 2

This example illustrates the preparation of the N-unsubstituted phosphonoxycarboxamides of this invention from the O-methyl O-carbomethoxymethyl methylphosphonate prepared in Example 1.

Fifty grams of anhydrous ammonia was dissolved in 700 ml. of methanol to prepare a 4.43 normal solution. 125 ml. of this solution was slowly added to the O-methyl carbomethoxymethyl methylphosphonate prepared in Example 1 at a temperature of 10°-15° C. This reaction mixture was then allowed to stand overnight at room temperature.

The next day, an additional 545 ml. of the 4.43 normal ammonia solution was added to the reaction mixture at reduced temperature followed by 220 ml. of a similarly prepared 9.3 molar ammonia solution. Following this addition, a 1.0 ml. sample of the reaction product was found to have 0.21 meq. ammonia (to bromothymol blue). The reaction mixture was heated to 46° C. for two hours after which it was found to contain 0.18 meq. ammonia/ml. and 0.4 meq. R N+H3/ml. The reaction product was then stripped of methanol to a final weight of 781 grams.

275 ml. of tetrahydrofuran and a few seed crystals were added to 760 grams of the stripped product. The resulting precipitate was filtered out and washed three times with butanol to yield 375 grams of crystalline product having a melting point of 40°-48° C. This product was recrystallized in 200 grams of ethanol and then washed with methyl-ethyl ketone to yield 210.5 grams of a crystalline product having a melting point of 50°-55° C. Infrared analysis of this product indicated that C=O and P=O were present in a 1:1 ratio.

EXAMPLE 3

This example illustrates the N- substitution of the phosphonoxycarboxamide prepared in Example 2.

200 grams of the phosphonoxycarboxamide prepared in Example 2 and 42 grams of paraformaldehyde (95 percent formaldehyde) were heated to 80° C. and stirred for one hour. All of the paraformaldehyde dissolved, indicating that reaction had taken place.

EXAMPLE 4

This example illustrates the preparation of a bis carbalkoxymethyl phosphonate precursor used in preparing the bis(carbamidomethyl) phosphonates of this invention.

167.5 grams of dimethyl methyl phosphonate was heated to 125° C. in a flask equipped with a stirrer, an overhead condenser, and a condensate trap. 0.5 gram of tetraethylammonium chloride was stirred in, and then 457 grams of ethyl bromoacetate was added over a period of about 2½ hours. As the ethyl bromoacetate was being added, the reaction temperature increased to a maximum of 170° C., and methyl bromide vapors were condensed in the overhead condenser and collected in the condensate trap. Upon completion of the addition of the ethyl bromoacetate to the flask, the reaction mixture was allowed to cool to room temperature. At this time, the condensate trap was found to contain 217.3 grams of methyl bromide. The flask contents were then reheated to a temperature ranging from about 162° C. to about 165° C. for about 1½ hours during which time an additional 14 grams of methyl bromide was collected in the condensate trap. Upon cooling, the flask was found to contain 394 grams of product in the form of a yellow fluid. This compares to a calculated (theoretical) yield of 368 grams.

EXAMPLE 5

This example illustrates the preparation of bis(carbamidomethyl) methylphosphonate from the bis (carbalkoxymethyl) methylphosphonate precursor prepared in Example 4.

Forty-seven grams of anhydrous ammonia was dissolved in ethanol to prepare 660 ml. of a 4.15 molar solution. This solution was then added at room temperature to the product of Example 4, with no observable exotherm resulting. The reaction mixture was allowed to stand in an ice bath for three days. When subsequently heated to 65° C. under a dry-ice dephlegmator, no ammonia condensed out; this was taken as an indication that the reaction had been completed. The reaction mixture was then stripped of ethanol under vacuum to a weight of 394 grams and then Hivac stripped to a final weight of 366 grams (compared to a theoretical weight of 290 grams). Infrared analysis indicated the presence of some remaining ester functionality. A sample of the reaction mixture was titrated to the thymolphthalein end point which indicated the presence of about 0.4 mole of NH4+. Seven grams of ammonia in 35 ml. of methanol was then added and the reaction mixture allowed to stand overnight at 43° C. Titration of a sample of the reaction mixture with acid indicated that the entire reaction mixture contained about 70 meq. NH3. The reaction mixture was then heated for 29 hours at a temperature ranging from 40°-45° C. Subsequent analysis indicated the presence of 25 meq. of ammonia.

The reaction mixture was then stripped of methanol at a temperature of 62° C. and a pressure of 0.1 mm. abs. to a final product weight of 345 grams.

EXAMPLE 6

This example illustrates the preparation of a flame retardant textile finish with the phosphonoxycarboxamides of this invention.

An aqueous padding bath was prepared containing 54.9 percent by weight of water, 0.1 percent by weight of "TRITON X-100", an ethoxylated tertiary-octylphenol condensate wetting agent sold by the Rohm and Haas Company, 30 percent by weight of N-methylol, O-methyl methylphosphonoxyacetamide (i.e.., Compound (2), 10 percent by weight of tris (methoxymethyl) melamine, an aminoplast obtained from the American Cyanamid Company under the tradename "AEROTEX 23 SPECIAL", and 5 percent by weight of ammonium chloride (as catalyst). A sample of cotton flannel cloth having a weight of 3.8 oz./sq. yard was padded through the aqueous padding bath and then dried at 250° F. (121.1° C.) for 1½ hours and cured at 350° F. (176.7° C.) for two hours. Dry add-on weight was found to be 24.2 percent by weight of untreated cloth.

The treated flannel cloth was then subjected to a series of ten hot water, i.e., 60° C., detergent washes in a home washing machine containing 50 grams of "Tide XK", a strong laundry detergent sold by the Proctor and Gamble Company, and 200 parts per million of water hardness (calculated as CaCO3 using Mg.(NO3)2.6H2O and Ca(NO3)2.4H2O) and eight bath towels as ballast.

The flammability of the cloth was evaluated before and after washing by means of a modified vertical char length test. In the vertical char length test, the complete details of which are described in the Federal Flammability Standard of July 27, 1971, (35 *Federal Register* 146), a 10-inch strip of the finished cloth is suspended vertically so that its lower edge is maintained ¾ inch (1.9CH) above the top of a Bunsen burner having a 1.5-inch (3.81 cm) high flame for a period of three seconds. The length of the resulting char, in inches, is then measured upward from the base of the strip. Thus, a shorter char length of about 3 to 5 (7.6 to 12.7 cm) is indicative of a greater degree of fire retardancy while a char length of about 10 inches (25.4 cm) (burned its entire length) is unacceptable for most applications. The hand and color of the cloth samples were also evaluated before and after washing. For this experiment, the drying conditions were modified to those given above, and an 8-inch strip of cloth was used instead of a 10-inch strip. The results of these evaluations were as follows:

|  | Vertical Char (inches) | Hand | Color |
| --- | --- | --- | --- |
| Before Washing | 4.25"(10.8cm) | 2.0 | Light Yellow |
| After Washing | 6.5" (16.5cm) | 1.5 | White |

EXAMPLE 7

This example illustrates the preparation of a flame retardant finish with a bis-phosphonoxycarboxamide of this invention.

An aqueous padding bath was prepared as in Example 6 except that the O-methyl methylphosphonoxyacetamide of Example 7 was replaced by a methylolated bis(carbamidomethyl) methylphosphonate, i.e., Compound (11). A sample of the same cotton flannel cloth as was used in Example 6 was padded through the aqueous padding bath, dried, and cured as in Example 6. Dry add-on weight was found to be 21.8 percent by weight of untreated cloth.

The treated cloth was washed and evaluated for flammability, hand, and color as in Example 6 with the following results:

|  | Vertical Char (inches) | Hand | Color |
| --- | --- | --- | --- |
| Before Washing | 4.5"(11.4 cm) | 2.0 | Brown |
| After Washing | *B.E.L. | 1 | Tan |

*Burned entire length.

It was found that the flame retardancy "before washing" produced by the bis (carbamidomethyl) methyl phosphonate was roughly equivalent to that of the monocarbamidomethyl methyl phosphonate of Example 6. The flame retardancy after washing 10 times was judged to be unacceptable. thus, either compound may be used to achieve effective flame retardancy in applications which are not subject to laundering; but for those applications subject to laundering, the mono-carbamidomethyl methyl-phosphonate should be used.

It may thus be seen that the novel phosphonoxycarboxamide compounds of this invention are effective in imparting flame retardance to textile materials. The novel flame-retardant compositions of this invention impart flame retardance to textile materials at reasonable add-on weights, thereby making them highly desirable for use in textiles from which light weight articles of clothing are to be manufactured. The textiles to be made flame retardant may be effectively and conveniently treated to impart flame retardance to them by the process of this invention. The objects set forth above, among those made apparent from the preceding description, are therefore effectively attained.

Since certain changes may be made in the above compounds, compositions, and process without departing from the scope of this invention, it is intended that all matter contained in the above description shall be interpreted as illustrative and not in a limiting sense.

What is claimed is:

1. A compound of the formula

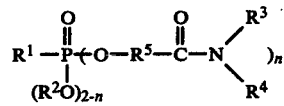

wherein $R^1$ and $R^2$ are selected from the group consisting of aryl and alkyl having from 1-6 carbon atoms and may be the same or different; $R^3$ represents hydrogen or $-CH_2OH$; $R^4$ represents hydrogen, $-CH_3$, $-CH_2OH$, or $-C_2H_4OH$, $R^5$ represents $-CH_2-$, and n represents 1 or 2.

2. A compound in accordance with claim 1 wherein $R^1$ represents an alkyl radical of from 1-4 carbon atoms, $R^2$ represents an alkyl radical of from 1-2 carbon atoms.

3. A compound in accordance with claim 1 wherein n is 1.

4. A compound in accordance with claim 3 wherein $R^1$ is methyl, $R^2$ is methyl, at least one of $R^3$ and $R^4$ is methylol, and $R^5$ is methyl.

5. A compound in accordance with claim 1 wherein n is 2.

6. A compound in accordance with claim 5 wherein $R^1$ is methyl, $R^2$ is methyl, and at least one of $R^3$ and $R^4$ is methylol.

* * * * *

UNITED STATES PATENT AND TRADEMARK OFFICE
CERTIFICATE OF CORRECTION

PATENT NO. : 4,162,279
DATED : July 24, 1979
INVENTOR(S) : Edward N. Walsh and Ralph B. Fearing It is certified that error appears in the above-identified patent and that said Letters Patent are hereby corrected as shown below:

Col. 2, line 13 - "1 r 2" should be "1 or 2".

Col. 4, line 40 -

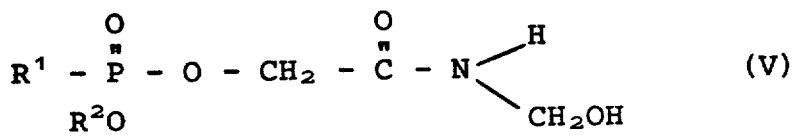

should be

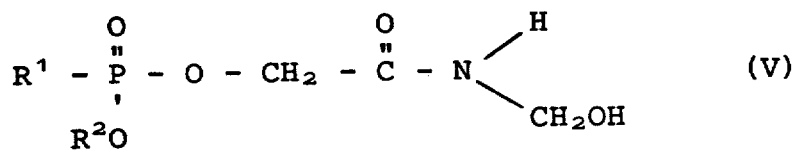

Col. 5, line 5 -

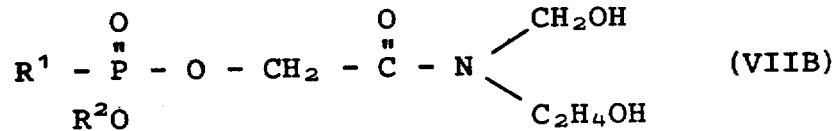

should be

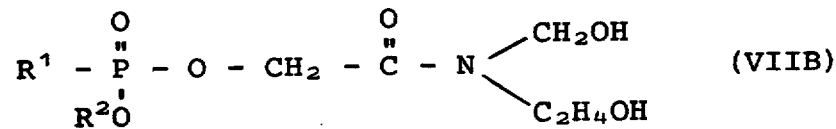

Col. 7, line 8 - "demethylolethylene" should be "dimethylolethylene"

Col. 8, line 9 - "structure" should be "substrate".

UNITED STATES PATENT AND TRADEMARK OFFICE
CERTIFICATE OF CORRECTION

PATENT NO. : 4,162,279
DATED : July 24, 1979
INVENTOR(S) : Edward N. Walsh and Ralph B. Fearing It is certified that error appears in the above-identified patent and that said Letters Patent are hereby corrected as shown below:

Col. 8, lines 42 and 43 - "enulsion" should be "emulsion".

Col. 10, line 5 - "phosphonates" should be "methylphosphonate".

Col. 12, line 17 - "thus" should be "Thus".

Signed and Sealed this

Eighteenth Day of December 1979

[SEAL]

Attest:

Attesting Officer

SIDNEY A. DIAMOND

Commissioner of Patents and Trademarks